United States Patent
Wu

(10) Patent No.: US 6,346,110 B2
(45) Date of Patent: Feb. 12, 2002

(54) CHAMBER FOR APPLYING THERAPEUTIC SUBSTANCES TO AN IMPLANTABLE DEVICE

(75) Inventor: Steven Z. Wu, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/754,619

(22) Filed: Jan. 3, 2001

Related U.S. Application Data

(62) Division of application No. 09/411,029, filed on Oct. 4, 1999, now Pat. No. 6,203,551.

(51) Int. Cl.[7] ................................................. A61F 11/00
(52) U.S. Cl. ............................................. 606/108; 606/1
(58) Field of Search ............................ 606/1, 191–198, 606/108; 604/103, 103.01, 103.02, 96.01, 53

(56) References Cited

U.S. PATENT DOCUMENTS

| | | | |
|---|---|---|---|
| 4,597,765 A | * 7/1986 | Klatt | 606/1 |
| 5,374,257 A | 12/1994 | Drainville et al. | 604/319 |
| 5,630,830 A | 5/1997 | Verbeek | 606/198 |
| 5,697,967 A | 12/1997 | Dinh et al. | 623/1 |
| 5,785,715 A | 7/1998 | Schatz | 606/108 |
| 5,833,651 A | 11/1998 | Donovan et al. | 604/53 |
| 6,009,614 A | * 1/2000 | Morales | 606/108 |

FOREIGN PATENT DOCUMENTS

| | | |
|---|---|---|
| EP | 0920843 | 6/1999 |
| WO | WO9857680 | 12/1998 |

\* cited by examiner

Primary Examiner—Kevin Truong
(74) Attorney, Agent, or Firm—Cameron, Kerrigan, Squire, Sanders & Dempsey, L.L.P.

(57) ABSTRACT

A chamber is provided that allows a user to medicate an implantable prosthesis such as a stent. The implantable prosthesis is capable of securing a therapeutic substance and subsequently delivering the therapeutic substance to local tissues. The chamber allows a user to medicate the prosthesis subsequent to the sterilization process and immediately prior to the implantation procedure. The chamber includes a hollow body defining a chamber cavity that encapsulates the prosthesis crimped on a balloon of a catheter assembly. The chamber is removably mounted on the catheter assembly. A user can supply therapeutic substances into the chamber and allow the therapeutic substances to be secured by the prosthesis. After allowing the prosthesis to be soaked by the therapeutic substances for a predetermined amount of time, the chamber is removed and the prosthesis is ready for the implantation procedure.

20 Claims, 3 Drawing Sheets

CHAMBER FOR APPLYING THERAPEUTIC SUBSTANCES TO AN IMPLANTABLE DEVICE

CROSS REFERENCE

This is a division of U.S. patent application Ser. No. 09/411,029 filed on Oct. 4, 1999 now U.S. Pat. No. 6,203, 551.

BACKGROUND OF THE INVENTION

1. Field of the Invention

This invention generally relates to implantable devices, such as an expandable intraluminal prosthesis commonly known as stents. More particularly, this invention relates to a structures and techniques for applying therapeutic substances to an implantable device in association with the implantation procedure.

2. Description of the Related Art

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable intraluminal prosthesis, an example of which includes a stent, is implanted in the lumen to maintain the vascular patency. A well known procedure for delivering the stent to the diseased site includes crimping a compressed stent about the balloon of the catheter such that when the balloon is inflated, the stent dilates and is disposed within the vasculature. FIG. 1 illustrates an example of the end result, the balloon having been deflated and withdrawn. FIG. 1 shows a stent 10, generally tubular in shape, in its expanded position, functioning to hold open and, if desired, to expand a segment of an anatomical lumen 12. As best shown by FIG. 1, stent 10 prevents torn or injured arterial lining 14 from occluding lumen 12.

In treating the damaged vasculature tissue and to further fight against thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient. Local medication delivery is a preferred method of treatment in that smaller total levels of medication are administered in comparison to systemic dosages, but are concentrated at a specific site. Local delivery thus produces fewer side effects and achieves more effective results. One commonly applied technique for the local delivery of the drugs is through the use of medicated stents. Stents that are capable of storing medication and releasing it at the implanted site are well known in the art. A metallic stent coated with a polymeric material which is impregnated with a drug or a combination of drugs is one example. Once the stent is implanted within the lumen, the drug(s) are released from the polymer. U.S. Pat. No. 5,605,696 to Eury et al., U.S. Pat. No. 5,464,650 to Berg et al., and U.S. Pat. No. 5,700,286 to Tartaglia et al. are examples illustrating the use of a polymeric coating for the local delivery of the drug(s).

Sterilization of medicated stents in preparation for stent therapy significantly limits the choice of drugs with which the stent can be medicated. More specifically, stents are sterilized by ethylene oxide (Eto) gas or electron beam radiation. Some therapeutic substances do not tolerate either the Eto or electron beam radiation procedure. Although some therapeutic substances tolerate Eto, Eto is the less preferred method of sterilization for coronary procedures since the procedure leaves an ethylene residue on the stent after sterilization, which can provoke an inflammatory response.

The available choice of therapeutic substances for medicating stents therefore includes substances that are not adversely affected by electron beam radiation. The selections are limited. Accordingly, it is desirable to medicate the stent subsequent to the sterilization procedure.

Medicated stents also inhibit a treating physician's ability to make an ad hoc selection of most suitable therapeutic substance or combination of therapeutic substances, and dosage for a particular patient. A physician cannot custom treat a stent according to a patient's needs, but rather is limited to selections that are already provided by a biomedical supplier. Accordingly, it is desirable to allow a physician to medicate the stent in accordance with the particular needs of a patient.

Stents are medicated by a biomedical supplier well in advance of the stent therapy procedure and supplied to users in sterile packages. The therapeutic substance concentration that is secured by the stent diminishes during storage in sterile packages due to inevitable diffusion of the substance from the stent. The time lapse between treating a stent with a therapeutic substance and implanting the stent may decrease the therapeutic substance's efficacy or require the package to be discarded if extending beyond the package expiration date. Accordingly, it is desirable to medicate a stent immediately prior to the stent therapy.

SUMMARY OF THE INVENTION

In accordance with various aspects of the present invention, a chamber is configured for usage with a catheter to apply one or more therapeutic substances to an implantable device such as a stent after sterilization but before implantation therapy. The chamber is configured to be mounted on a catheter assembly having a balloon portion and a stent crimped or mounted on the balloon portion. The chamber comprises a hollow body defining a chamber cavity, which encapsulates the stent. The chamber includes an inlet duct and an outlet duct which allow a user to supply therapeutic substance(s) into the chamber cavity and to discharge the therapeutic substance(s) out of the chamber cavity.

In one embodiment, the hollow body includes a first end and a second end opposing the first end, the first end having an aperture and a sealing member disposed on a periphery of the aperture.

In another embodiment, the second end additionally has an aperture and a sealing member on a periphery of the aperture.

In another embodiment, the hollow body of the chamber includes an upper chamber body and a lower chamber body. The upper and lower chamber bodies can be releasably secured together to form the chamber cavity.

Another aspect of the present invention is a method of medicating the stent by supplying a therapeutic substance into the chamber cavity wherein the substance is exposed to or soaks the stent. The therapeutic substance is trapped in the chamber cavity and discharged after a predetermined period of time. Alternatively, the therapeutic substance is immediately discharged as it is supplied into the chamber cavity, creating a continuous flow through the chamber cavity. The continuous flow is maintained for a predetermined amount of time. The stent used in conjunction with the chamber of the present invention should be capable of storing or securing the therapeutic substance(s) and releasing the substance (s) at the site of treatment.

DETAILED DESCRIPTION OF THE PREFERRED EMBODIMENTS

Figure 1:
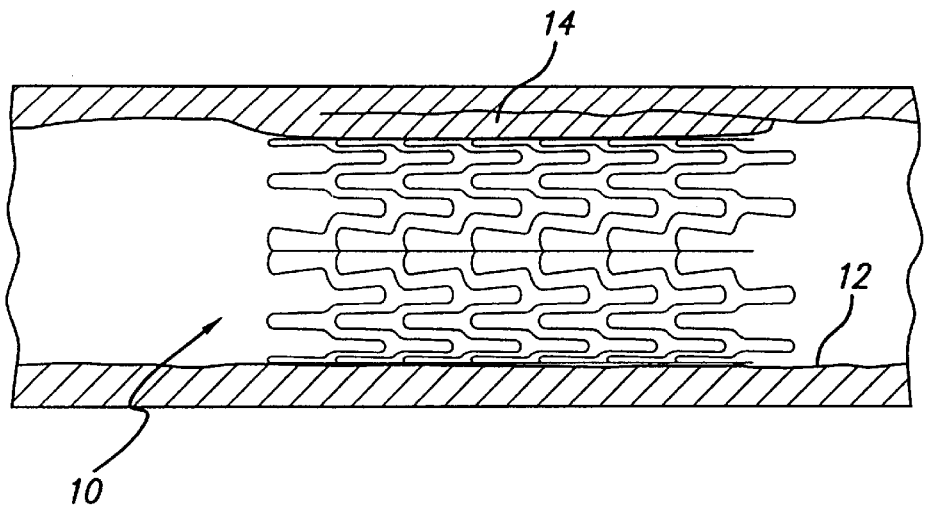
FIG. 1 illustrates an expanded stent within a vessel after withdrawal of a catheter assembly.
Figure 2:
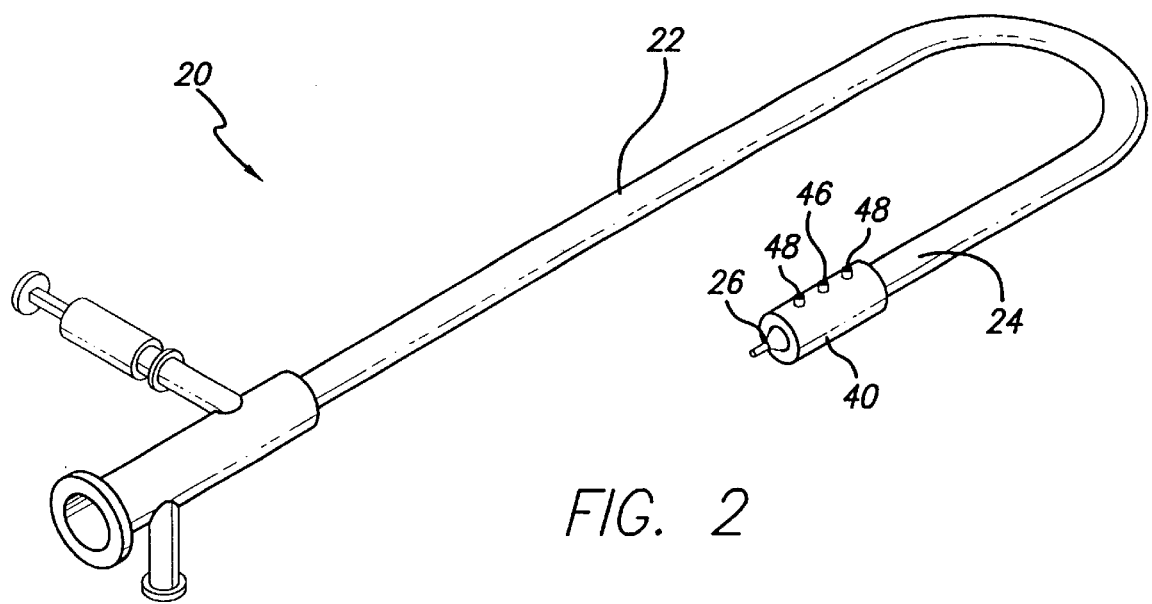
FIG. 2 is a prospective view of a catheter assembly having a chamber mounted thereon in accordance with one embodiment of the invention.

Referring to the drawings, wherein similar parts are identified by like reference numeral, FIG. 2 illustrates a chamber 40 that is configured for usage with a catheter assembly 20. The catheter assembly 20 can be any conventional catheter assembly that is well known and used in a variety of medical procedures such as percutaneous transluminal coronary angioplasty (PTCA), vascular prosthetic implantation, and atherectomy.

Catheter assembly 20 includes catheter tube 22 having a distal end 24 and a balloon 26 incorporated proximal to distal end 24. Balloon 26 is inflatable to dilate from a collapsed configuration to an expanded configuration. Balloon 26 is selectively deflatable after inflation to return to the collapsed configuration. Balloon 26 can be fabricated, for example, from a flexible polymer such as nylon, polyethylene, or polyethylene terephthalate. The illustrative balloon 26 is adapted for inserting and dilating an implantable device or an expandable prosthesis 28 (see FIG. 3), e.g., a stent. The selection of a particular balloon-catheter assembly 20 is not critical so long as the assembly 20 is capable of and suitable for delivering implantable device 28.

As further illustrated in FIGS. 2–5 chamber 40 is provided that allows a user such as a physician to medicate stent 28 immediately prior to implantation procedure. Chamber 40 is removably mounted on balloon 26 and encapsulates stent 28. Chamber 40 is generally defined by a hollow, tubular body 42 defining a chamber cavity 44. Chamber 40 has an inlet duct 46 and a pair of outlet ducts 48. Inlet duct 48 and outlet ducts 48 are typically apertures, conduits or tubes expanding out of tubular body 42. Inlet duct 46 and outlet ducts 48 are typically open passageways or closed passageways that are capable of penetration by a syringe. Alternatively, inlet duct 46 and outlet ducts 48 can be open passageways sealed by removable caps (not illustrated). In various embodiments chamber 40 can have any number of inlet ducts 46 and outlet ducts 48 and extend beyond the specific structure shown in FIGS. 2–5. Tubular body 42 has a pair of opposing ends 50 and 52 having apertures 53A and 53B formed therein. A pair of sealing members 54A and 54B, illustratively "O" rings, are disposed about the periphery of apertures 53A and 53B, respectively. Sealing members 54A and 54B seal chamber 40 against balloon 26 and prevent significant leakage of fluids or gases out of chamber cavity 44. Chamber 40 is generally capable of insertion onto and removal from catheter assembly 20 by threading and retracting distal end 24 of catheter assembly 20 through apertures 53A and 53B. Sealing members 54A and 54B facilitate sliding of the chamber 40 onto balloon 26 and off balloon 26 to prevent significant variation or disturbance to the positioning of stent 28 and prevent damage to the structure of stent 28.

Figure 4:
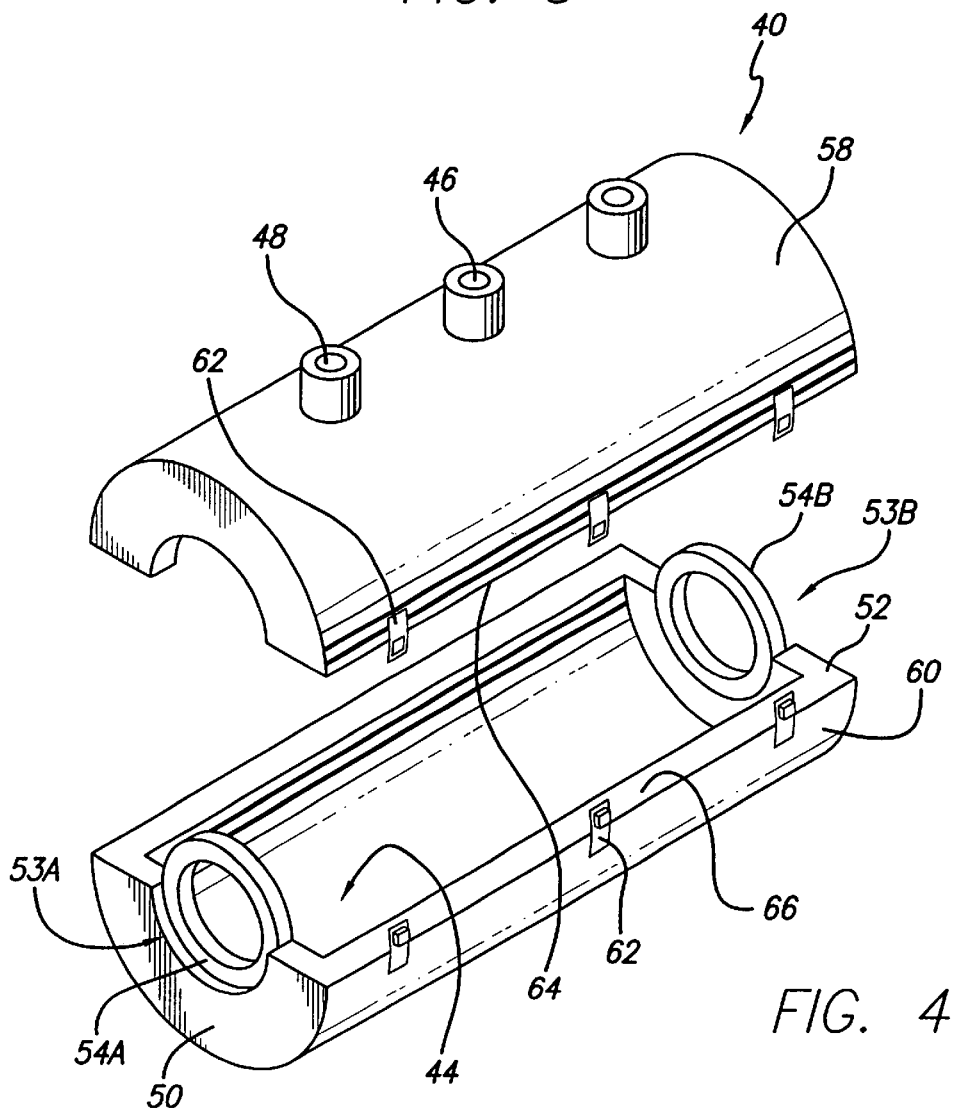
FIG. 4 is a prospective view of the chamber in accordance with another embodiment of the present invention.
Figure 5:
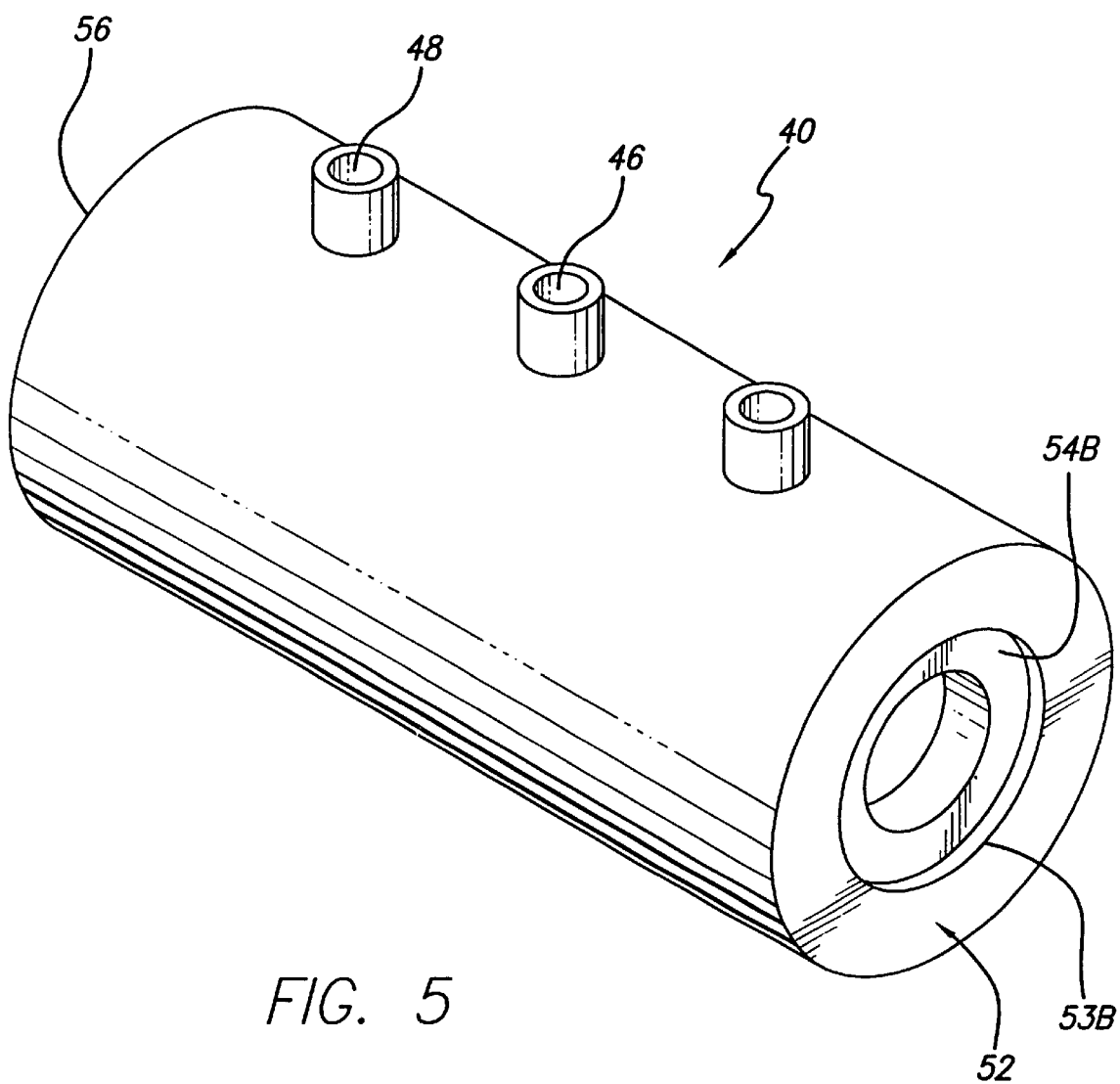
FIG. 5 is a side view of the chamber in accordance with another embodiment of the present invention.

An alternative embodiment is illustrated in FIG. 4 in which chamber 40 includes an upper chamber body 58 and a lower chamber body 60 which are configured to mate to form chamber cavity 44. Latching members 62 are disposed about the periphery of upper and lower chamber bodies 58 and 60, and are used to releasably lock upper chamber body 58 against lower chamber body 60. Stent 28 is encapsulated by positioning balloon 26 between upper and lower chamber bodies 58 and 60 and securely mating the upper and lower chamber bodies 58 and 60 to one another. The encapsulation method is more suitable for preventing significant disturbance to the positioning of stent 28 and damage to structure of the stent than the method of sliding chamber 40 on and off balloon 26. Other conventional articles, such as screws, may alternatively be used to secure upper chamber body 58 to lower chamber body 60. A sealing member (not illustrated) may be disposed about lips 64 and 66 of upper and lower chamber bodies 58 and 60 to prevent significant leakage of fluids or gases from chamber cavity 44.

Chamber 40 is fabricated from any suitable material that does not react adversely or erode when in contact with therapeutic substances or the solvents carrying such substances. Alternatively, the inside surfaces of chamber cavity 44 can be coated with a suitable material for preventing pollution or degradation of therapeutic substances that are introduced into chamber cavity 44. By way of example and not limitation, chamber 40 may be fabricated from any suitable polymer, such as a polytetrafluoroethylene or high density polyethylene. Chamber 40 may also be fabricated from a metallic material such as aluminum or stainless steel. It is understood that chamber 40 can be of any suitable size and can have a variety of suitable shapes, other than tubular body 42 illustrated in FIGS. 2–5. As further illustrated in FIG. 5, chamber 40 can have a closed end 56 in lieu of aperture 53A of end 50.

In an illustrative commercial kit, catheter assembly 20 with implantable device 28 (for example, stent) are sterilized and packaged in combination with chamber 40 removably encapsulating implantable device 28, for usage by a user such as a physician. The user removes the combined catheter assembly 20 and mounted chamber 40 from the sterile commercial kit immediately prior to the implantation therapy and uses chamber 40 to medicate stent 28 according to the individual requirements of the patient. The user then removes chamber 40 from balloon 26, and performs the implantation procedure.

In an alternative commercial embodiment, catheter assembly 20 and chamber 40 are packaged in separate sterile kits. A user removes the sterilized catheter assembly 20 and chamber 40 from respective sterile kits. The user encapsulates balloon 26 within chamber 40 and medicates stent 28. The user then removes chamber 40 from balloon 26 and performs the implantation procedure. In various embodiments, catheter assembly 20 may be provided having stent 28 mounted on the assembly 20, or stent 28 may be provided in a separate sterile kit. In cases with separate packaging for catheter assembly 20 and stent 28, the user crimps stent 28 onto the balloon 26 prior to usage.

In further additional commercial embodiments, chamber 40, catheter assembly 20 and stent 28 may be provided in non-sterile kits in which case all articles are sterilized prior to the treatment of a patient.

As described hereinafter with reference to Examples 1–4, stent 28 is medicated by introducing a solution of a therapeutic substance into chamber 40 encasing stent 28 through inlet duct 46 so that the therapeutic substance is in contact with stent 28. According to a first illustrative technique, the solution is trapped in chamber cavity 44 by closing outlet duct 48. Stent 28 is soaked for a predetermined period of time, then the solution is discharged from chamber cavity 44.

Alternatively, the therapeutic solution is introduced to chamber 40 via inlet duct 46 with outlet duct 48 left open so that the solution continuously flows through chamber cavity 44. The medicated solution simultaneously discharges from outlet duct 48 substantially at the rate the solution is supplied through inlet duct 46. Stent 28 is thus exposed to the continuous flow or soaked by the medicated solution for a predetermined period of time. In some applications a second solution such as a medicated solution, an aqueous solution, water, or the like can be supplied through the chamber 40 following application of the first solution. The type of medicated solution, the number of solutions applied, the dosages, dosage rates, concentrations of the solutions, and the duration of exposure or soaking depend on the type of stent and the therapy applied to the patient. Similarly, the therapy parameters are interrelated so that the dosages, dosage rates, and durations of exposure depend on the therapeutic substances, solvents, duration of the local therapy, rate of release, and the cumulative amount of release that is desired. Correlations and interrelations between therapy parameters are well known in the art and are easily calculated.

As discussed in the Background of the Invention, sterilization of a stent after the stent is medicated but before stent therapy limits the choice of drugs with which stent can be medicated since many therapeutic drugs do not tolerate conventional ethylene oxide (Eto) gas or electron beam radiation sterilization procedures. Chamber 40 advantageously allows a user to change the order of sterilization and medication of a stent so that the stent is first sterilized, then medicated, before usage as an implant. Chamber 40 thus expands the selection of therapeutic substances that are available to the physician to substances that are adversely affected by electron beam radiation. Chamber 40 also allows the physician to treat a subject more effectively. In other words, the physician can select on an ad hoc basis the most suitable therapeutic substance or combination of substances and the dosage(s) in accordance with the particular needs of a subject.

Examples in the expanded list of therapeutic substances or agents used in conjunction with chamber 40 include, but are not limited to, antineoplastic, anti-inflammatory, antiplatelet, anticoagulant, fribrinolytic, thrombin inhibitor, antimitotic, and antiproliferative substances. Examples of antineoplastics include paclitaxel and docetaxel. Examples of antiplatelets, anticoagulants, fribrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of suitable antimitotic agents include methotrexate, azathioprine, vincristine, vinblastine, flurouracil, adriamycin, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. While the foregoing therapeutic substances or agents are well known for their preventative and treatment purposes, they are provided by way of example and are not meant to be limiting. Other therapeutic substances which are currently available or may be developed are equally applicable for use with the present invention. The treatment of patients using the above mentioned medicines is well known in the art.

Figure 3:
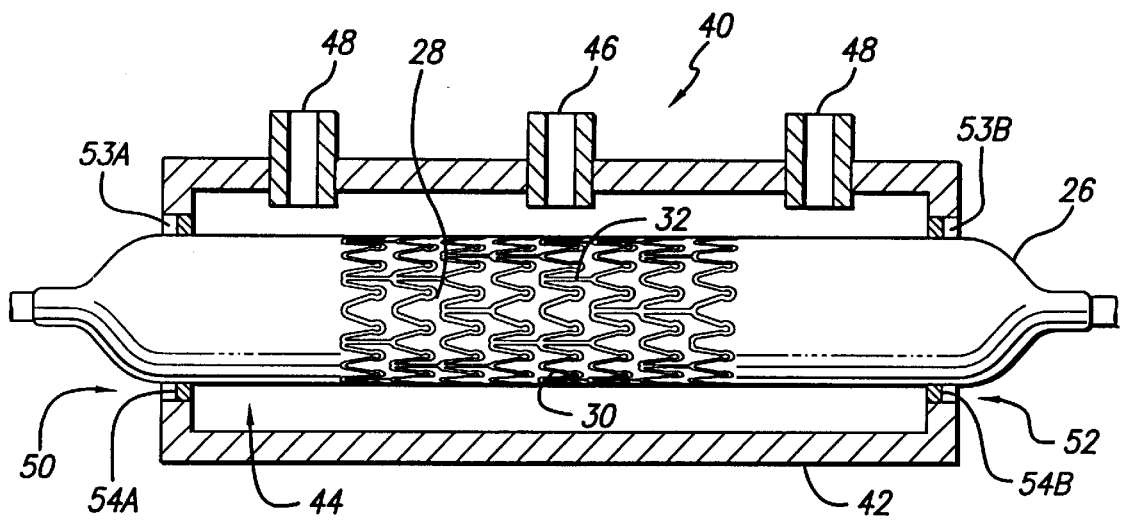
FIG. 3 is a cross-sectional view of the chamber, encapsulating a stent crimped on a balloon of the catheter assembly.

Referring to FIG. 3, stent 28 is crimped on balloon 26 in a compressed configuration. Stent 28 is defined by a plurality of radially expandable cylindrical elements 30 disposed coaxially and interconnected by connecting elements 32. Connecting elements 32 are disposed between adjacent cylindrical elements 30. Cylindrical 30 and connecting 32 elements can be fabricated from a metallic material or an alloy such as stainless steel (e.g., 316L), "MP35N," "MP20N," tantalum, nickel-titanium alloy (commercially available as Nitinol®), platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. It is understood, however, that the underlying structure of stent 28 can be virtually any stent design. It is further understood the aforementioned list is merely an exemplary list of materials that can be used and that other materials, such as polymeric materials, have been proven to function effectively. Examples of polymeric material include, poly(ethylene terephthalate), polyacetal, poly(lactic acid), and poly (ethylene oxide)/poly(butylene terephthalate) copolymer.

A suitable stent 28 used in conjunction with chamber 40 is a stent that stores or secures therapeutic substance(s) and allow the substance(s) to be released at the implanted site for a predetermined duration of time. Stents that are capable of being impregnated with or securing therapeutic substance(s) and locally releasing such substance(s) for a predetermined duration of time are illustrated by the following set of examples by way of example only and not by way of limitation. The structure of the stents, the materials used, and the method of storing or securing therapeutic substance(s) on to the stent should not be construed to limit the scope of the invention.

EXAMPLE 1

An illustrative stent 28 is a bare metallic stent such that the metallic substrate is capable of absorbing or attaching to therapeutic substance(s). To medicate stent 28, the metallic substrate of stent 28 is exposed to or soaked with a solvent carrying a therapeutic substance by supplying the solution through inlet duct 46 of chamber 40. The therapeutic substance is dispersed throughout the solvent in a true solution with the solvent and not dispersed in fme particles. The medicated solution absorbs or attaches to the metallic substrate and is released in vivo after stent 28 is implanted. A suitable exposure of the metallic substrate to the solvent does not adversely alter the composition or characteristics of the therapeutic substance. Examples of some suitable combinations of metallic substrates, solvents, and therapeutic substances are set forth in Table I. Table I is an exemplary list of a few suitable combinations, and it is understood that many ther combinations can be practiced with chamber 40.

TABLE I

| Metallic Substrate | Solvent | Therapeutic Substance |
|---|---|---|
| Stainless Steel (e.g., 316L) | ethanol | dexamethasone |
| Stainless Steel (e.g., 316L) | chloroform | dexamethasone |
| Stainless Steel (e.g., 316L) | methyl alcohol | taxol |
| Nitinol ™ | water | aspirin |
| Nitinol ™ | water | heparin |

Therapeutic parameters such as dosages, dosage rates, concentration of the solution, and the duration of exposure depend on various factors including metallic substrate type, particular selected therapeutic substance, particular selected solvent, and the duration of the local release, the cumulative amount of release, and the rate of release that is desired. Correlations and interrelations between therapeutic parameters are well known in the art and are easily calculated.

EXAMPLE 2

For some illustrative catheters the metallic material from which stent 28 is made include a plurality of porous cavities, as disclosed in U.S. Pat. No. 5,843,172 to John Y. Yan, which is incorporated herein by reference in its entirety. The porous cavities of stent 28 are typically formed by sintering the stent material from metallic particles, filaments, fibers or other materials as disclosed in Yan. As a result, a therapeutic substance is loaded directly into the cavities. To load the cavities, stent 28 is soaked by supplying a solvent carrying a therapeutic substance into chamber cavity 44. The substance is dispersed throughout the chamber cavity 44 either in a true solution with the solvent, or dispersed in fine particles in the solvent. The medicated solute or the fine particles impregnate the cavities and are generally released in vivo over a desired period of time. Therapeutic parameters such as dosages, dosage rates, concentration of the solution, size of the particles if not in true solution, and the duration of exposure depend on various factors including size of the cavities, particular selected therapeutic substance, particular selected solvent, and the duration of the local release, the cumulative amount of release, and the rate of release that is desired. Correlations and interrelations between therapeutic parameters are well known in the art and are easily calculated.

EXAMPLE 3

In another example, stent 28 has a coating of a polymeric material capable of carrying and releasing the therapeutic substance. Polymeric material for carrying therapeutic substances are well known and practiced in the art. In order to medicate stent 28, chamber 40 is used to soak the polymeric coating with a solvent carrying a therapeutic substance. The substance is dissolved throughout the solvent to form a true solution with the solvent. The medicated solute absorbs into the micropores or matrices of the polymer and is capable of being released, in situ, over a predetermined period of time. The polymeric material is preferably a biocompatible material such as one or more polymers which, in the amounts employed, are non-toxic, non-inflammatory, chemically inert, and substantially non-immunogenetic. The polymer may either be bioabsorbable or biostable. A bioabsorbable polymer biodegrades or breaks down in the body and does not remain present long after implantation to cause any adverse local response. Bioabsorbable polymers are gradually absorbed or eliminated by the body by hydrolysis, metabolic process, bulk or surface erosion, or similar processes. Examples of bioabsorbable, biodegradable materials include, but are not limited to, polycaprolactone (PCL), poly-D, L4actic acid (DL-PLA), poly-L-lactic acid (L-PLA), poly(lactide-co-glycolide), poly (hydroxybutyrate), poly(hydroxybutyrate-co-valerate), polydioxanone, polyorthoester, polyanhydride, poly (glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as fibrin, fibrinogen, cellulose, starch, and collagen may also be suitable. Examples of biostable polymers include Parylene®, Parylast®, polyurethane (e.g., segmented polyurethanes such as Biospan®), polyethylene, polyethlyene teraphthalate, ethylene vinyl acetate, silicone and polyethylene oxide. It is essential for the polymeric coating not to dissolve when exposed to the solvent. It is also essential for the exposure of the solvent to the polymer not to adversely alter the therapeutic substance's composition or characteristic. Examples of suitable combinations of polymers, solvents, and therapeutic substances are depicted in Table II. Table II is an exemplary list of a few suitable combinations, and it is understood that many other combinations can be practiced with chamber 40.

TABLE II

| Polymer | Solvent | Therapeutic Substance |
|---|---|---|
| paralene | water | IIb/IIIa receptor antibody (e.g., ReoPro ®) |
| silicone | chloroform | dexamethasone |
| silicone | ethanol | dexamethasone |
| silicone | chloroform | aspirin |
| urethane | none | liquid form Vitamin E |
| urethane | dimethylsulfoxide (DMSO) | vinblastine |

Therapeutic parameters such as dosages, dosage rates, concentration of the solution, and the duration of exposure depend on various factors including particular selected polymeric coating, particular selected therapeutic substance, particular selected solvent, and the duration of the local release, the cumulative amount of release, and the rate of release that is desired. Correlations and interrelations between therapeutic parameters are well known in the art and are easily calculated.

EXAMPLE 4

For polymeric carriers that are impregnated with a therapeutic substance by a simple soaking operation, the duration of release of the therapeutic substance from the polymeric carrier is substantially equal to the time of exposure of the carrier. For example, a two (2) hour soaking of the polymeric carrier has an equivalent two (2) hour duration of in vivo release.

Typically it is advantageous to prolong the duration of in vivo release to days or weeks, but impracticable and undesirable to use chamber 40 to soak the polymeric carrier with a medicated solution for such time durations. Accordingly, polymers that are susceptible to swell loading or post-loading are advantageously used to increase the release duration. Swell loading or post-loading are well understood and practiced in the art. In a conventional and well known swell loading method, the polymeric carrier is soaked with a therapeutic substance/solvent solution. A suitable solvent is capable of not only carrying (i.e., not adversely affecting the therapeutic substance's characteristics or chemically altering the substance, and the substance should be capable of dissolving in the solvent) the therapeutic substance, but causing the polymer to swell. Optimal loading of the substance is obtained when the substance is highly soluble in the solvent, for example, when the substance is saturated in the solvent. Super-saturation of the solute is not desirable. Swelling of the polymeric carrier causes a higher quantity of the substance solute to diffuse into the matrices of the polymer in a shorter duration of time than by simply soaking a polymer that is not susceptible to swell loading.

Swell loading of a polymeric carrier using chamber 40 involves supplying a solution carrying a therapeutic substance into chamber cavity 44. The solution can be either an aqueous solution or a non-aqueous solution. A solvent which causes the greatest amount of swelling with the particular polymer is most advantageously chosen. After soaking stent 28 with either an aqueous or a non-aqueous solution, chamber 40 is removed and stent 28 is rapidly dried for example by exposure to mild heat for several minutes. The rapid removal or drying of the solvent from the polymeric carrier causes the polymer to collapse, trapping a high concentration of the substance into the polymer's matrices.

Alternatively, if a non-aqueous solution is used, water can be supplied into chamber cavity 44 to rinse the polymeric carrier. Water precipitates the therapeutic substance and collapses the polymer. If water is used to collapse the polymer, a water-miscible solvent is generally most suitable. A suitable polymer does not dissolve when exposed to the solvent. A suitable combination of solvent and polymer does not chemically alter the composition of the substance or adversely affect the substance characteristics. Examples of some suitable combinations of polymers, solvents, and therapeutic substances are set forth in Table imi. Table III is an exemplary list of a few suitable combinations. Other combinations are also suitable for usage with chamber 40.

TABLE III

| Polymer | Solvent | Therapeutic Substance |
| --- | --- | --- |
| TecoGel ® (manufactured by Thermedics) | water | IIb/IIIa receptor antibody (e.g., ReoPro ®) |
| Tecophilic ® (manufactured by Thermedics) | water | aspirin |
| Tecophilic ® | chloroform | dexamethasone |
| polyvinyl alcohol | chloroform | dexamethasone |
| polyvinyl alcohol | water | heparin |

Therapeutic parameters such as dosages, dosage rates, concentration of the solution, and the duration of exposure depend on various factors including particular selected polymer, particular selected therapeutic substance, particular selected solvent, and the duration of the local release, the cumulative amount of release, and the rate of release that is desired. Correlations and interrelations between therapeutic parameters are well known in the art and are easily calculated.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of medicating a prosthesis prior to implanting said prosthesis in a subject, comprising the acts of:
    (a) providing a catheter assembly, a balloon disposed on said catheter assembly, a prosthesis mounted on said balloon, and a chamber encapsulating said prosthesis; and
    (b) supplying a therapeutic substance into said chamber, wherein said therapeutic substance is secured by said prosthesis and is capable of being released after said prosthesis is implanted in a subject.

2. The method of claim 1, additionally comprising the act of sterilizing said prosthesis prior to said act of supplying said therapeutic substance into said chamber.

3. The method of claim 2, wherein said act of sterilizing is performed by electron beam radiation.

4. The method of claim 1, wherein said act of providing comprises removing said catheter assembly having said balloon, said prosthesis mounted on said balloon, and said chamber encapsulating said prosthesis from a package.

5. The method of claim 1, wherein said act of providing comprises removing said catheter assembly having said balloon and said prosthesis mounted on said balloon from a first package, removing said chamber from a second package, and mounting said chamber on said catheter assembly.

6. The method of claim 1, wherein said act of providing comprises removing said catheter assembly having said balloon from a first package, removing said prosthesis from a second package, crimping said prosthesis on said balloon, removing said chamber from a third package, and mounting said chamber on said catheter assembly.

7. The method of claim 1, wherein said act of supplying a therapeutic substance into said chamber comprises adding said therapeutic substance to a fluid and supplying said fluid into said chamber.

8. The method of claim 1, wherein during said act of supplying, said therapeutic substance is not discharged from said chamber as it is being supplied into said chamber.

9. The method of claim 8, additionally comprising the act of discharging said therapeutic substance from said chamber after a predetermined period of time.

10. The method of claim 1, wherein during said act of supplying, said therapeutic substance is discharged out of said chamber as it is being supplied into said chamber, said therapeutic substance is supplied for a predetermined period of time.

11. The method of claim 1, additionally including the act of removing said chamber from said catheter assembly subsequent to exposing said therapeutic substance to said prosthesis for a predetermined period of time.

12. The method of claim 1, additionally including the act of implanting said prosthesis in a subject.

13. The method of claim 1, wherein said therapeutic substance is selected from a group of antineoplastic, antiplatelet, anticoagulant, fribrinolytic, antimitotic, thrombin inhibitor, antiinflammatory and antiproliferative substances.

14. A method of preparing a radially expandable stent for an implantation procedure, comprising the act of:

supplying a substance into a chamber encapsulating a radially expandable stent, wherein said radially expandable stent has been sterilized in preparation for implantation procedure and is in at least a partially compressed configuration in said chamber, said stent is capable of securing said substance for delivery of said substance when said stent has been implanted in a vessel of a subject.

15. The method of claim 14, wherein said substance is supplied by a fluid carrier into said chamber and wherein said fluid carrier is discharged out from said chamber as said fluid carrier is supplied into said chamber.

16. The method of claim 14, wherein said substance is supplied by a fluid carrier into said chamber and wherein during said act of supplying said fluid carrier is contained in said chamber for a predetermined duration of time without any significant discharge out from said chamber.

17. The method of claim 16, wherein said fluid carrier is discharged out from said chamber after said predetermined duration of time.

18. A method of preparing a stent for an implantation procedure, comprising the acts of:

(a) providing a stent which has been sterilized in preparation for an implantation procedure; and (b) supplying a substance into a chamber encapsulating said stent, wherein said stent secures said substance for delivery of said substance when said stent has been implanted in a vessel of a subject, wherein the act of providing comprises obtaining a kit containing said stent secured on a balloon of a catheter assembly.

19. A method of preparing a stent for an implantation procedure, comprising the acts of:

(a) releasably securing a chamber on a catheter assembly to encapsulate said stent; and (b) supplying a substance into a chamber encapsulating said stent, wherein said stent secures said substance for delivery of said substance when said stent has been implanted in a vessel of a subject.

20. A method of preparing a stent for an implantation procedure, comprising the act of:

supplying a substance into a chamber encapsulating a stent, wherein said stent secures said substance for delivery of said substance when said stent has been implanted in a vessel of a subject, wherein said chamber comprises: a hollow body defining a chamber cavity, and an inlet disposed in said hollow body for allowing a user to supply said substance into said chamber cavity, wherein said substance contacts said stent.

* * * * *